(12) United States Patent
Morard et al.

(10) Patent No.: US 12,315,167 B2
(45) Date of Patent: May 27, 2025

(54) 3D INTERACTIVE ANNOTATION USING PROJECTED VIEWS

(71) Applicant: GE Precision Healthcare LLC, Wauwatosa, WI (US)

(72) Inventors: Vincent Morard, Auvergne-Rhône-Alpes (FR); Jorge Hernandez Londono, Yvelines (FR); Nicolas Gogin, Hauts-de-seine (FR)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 191 days.

(21) Appl. No.: 18/156,971

(22) Filed: Jan. 19, 2023

(65) Prior Publication Data
US 2024/0249414 A1 Jul. 25, 2024

(51) Int. Cl.
 G06T 7/11 (2017.01)
 G06T 15/08 (2011.01)
 G16H 30/40 (2018.01)
(52) U.S. Cl.
 CPC ............... *G06T 7/11* (2017.01); *G06T 15/08* (2013.01); *G16H 30/40* (2018.01);
 (Continued)
(58) Field of Classification Search
 CPC ....... G06T 7/11; G06T 15/08; G06T 2200/04; G06T 2200/24; G06T 2207/10024; G06T 2207/10081; G06T 2207/10088; G06T 2207/20021; G06T 2207/20104; G06T 2207/30004; G06T 2210/41; G06T 2207/30008; G06T 2207/30101; G06T 7/174; G16H 30/40
 See application file for complete search history.

(56) References Cited

U.S. PATENT DOCUMENTS 8,155,405 B2 * 4/2012 Unal ..................... G06T 7/149
 382/128
10,394,416 B2 * 8/2019 Jeon ....................... G16H 50/20
 (Continued)

FOREIGN PATENT DOCUMENTS

FR 3027423 A1 4/2016

OTHER PUBLICATIONS

Wang, X. et al., "The SEM Statistical Mixture Model of Segmentation Algorithm of Brain Vessel Image," Lecture Notes In Computer Science, vol. 22, No. 11, Aug. 2010, 9 pages.
(Continued)

*Primary Examiner* — Motilewa Good-Johnson
(74) *Attorney, Agent, or Firm* — McCoy Russell LLP

(57) ABSTRACT

Various methods and systems are provided for image data segmentation. In one example, a method includes receiving a first segmentation input selecting a first set of pixels of a two-dimensional (2D) projected rendering, the 2D projected rendering generated from a 3D medical image dataset, retropropagating the selected first set of pixels to 3D space based on a mapping between the 2D projected rendering and the 3D medical image dataset to form a 3D segmentation mask, and saving the 3D segmentation mask in memory and/or applying the 3D segmentation mask to the 3D medical image dataset, wherein the 2D projected rendering is an intensity projection rendering.

20 Claims, 9 Drawing Sheets
(4 of 9 Drawing Sheet(s) Filed in Color)

(52) U.S. Cl.
CPC ...... *G06T 2200/04* (2013.01); *G06T 2200/24* (2013.01); *G06T 2207/10024* (2013.01); *G06T 2207/10081* (2013.01); *G06T 2207/10088* (2013.01); *G06T 2207/20021* (2013.01); *G06T 2207/20104* (2013.01); *G06T 2207/30004* (2013.01); *G06T 2210/41* (2013.01)

(56) References Cited

U.S. PATENT DOCUMENTS

| | | | | |
|---|---|---|---|---|
| 10,600,184 | B2* | 3/2020 | Golden | G06T 7/149 |
| 10,672,115 | B2* | 6/2020 | Panda | G06T 7/90 |
| 10,803,588 | B2* | 10/2020 | Zhao | G06T 7/0016 |
| 11,049,289 | B2 | 6/2021 | Morard et al. | |
| 11,227,683 | B2* | 1/2022 | Morard | G06T 7/0014 |
| 2003/0197704 | A1* | 10/2003 | Tek | G06T 17/00 345/474 |
| 2009/0052756 | A1* | 2/2009 | Saddi | G06V 10/7553 382/131 |
| 2010/0316277 | A1* | 12/2010 | Fan | G06T 7/33 382/128 |
| 2011/0235891 | A1 | 9/2011 | Sonnemans et al. | |
| 2012/0293514 | A1* | 11/2012 | Virtue | G06T 7/174 345/419 |
| 2013/0021372 | A1* | 1/2013 | Wiemker | G06T 7/0012 382/128 |
| 2014/0037177 | A1* | 2/2014 | Endo | G06T 11/00 382/131 |
| 2014/0104273 | A1* | 4/2014 | Otsuna | G06T 7/11 345/423 |
| 2016/0217568 | A1* | 7/2016 | Vancamberg | G06T 7/0012 |
| 2016/0300343 | A1* | 10/2016 | Gazit | G06T 7/0014 |
| 2018/0247199 | A1* | 8/2018 | Cox | G06N 3/084 |
| 2018/0338740 | A1* | 11/2018 | Behrooz | G06T 7/13 |
| 2019/0066294 | A1* | 2/2019 | Yu | G06T 7/143 |
| 2019/0088004 | A1* | 3/2019 | Lucas | G06T 19/20 |
| 2019/0287234 | A1* | 9/2019 | Panda | G06T 7/136 |
| 2020/0380675 | A1* | 12/2020 | Golden | G06T 7/143 |
| 2021/0027098 | A1* | 1/2021 | Ge | G06F 18/217 |
| 2021/0110533 | A1* | 4/2021 | Viti | G06N 3/045 |
| 2022/0133278 | A1* | 5/2022 | Sheeran | A61B 8/0866 600/443 |
| 2022/0230310 | A1* | 7/2022 | Xie | G06V 10/764 |
| 2023/0342940 | A1* | 10/2023 | Shen | G06T 7/187 |
| 2024/0087218 | A1* | 3/2024 | Petkov | G16H 30/40 |
| 2024/0249414 | A1* | 7/2024 | Morard | G06T 15/08 |
| 2024/0312581 | A1* | 9/2024 | Colley | G16H 50/50 |

OTHER PUBLICATIONS

Dufour, A. et al., "From 2D markers in MIP to 3D vessel segmentation: A fuzzy paradigm for connected filtering," Proceedings of the 2013 IEEE 10th International Symposium on Biomedical Imaging, Apr. 7, 2013, San Francisco, CA, 4 pages.

Lamy, J. et al., "Preliminary results with a new annotation tool for liver volume and inner vessels from DCE-MRI data," HAL Science Website, Available Online at https://hal.science/hal-02537919/file/Lamy%20VPH%202020%202.pdf, Apr. 9, 2020, 3 pages.

"Guide To labelCloud: A Python Tool for Annotating 3D Point Clouds," Analytics India Mag Website, Retrieved from WayBack Machine Internet Archive Website, Available Online at https://web.archive.org/web/20210513093018/https://analyticsindiamag.com/labelcloud-python-tool-for-annotating-3d-point-clouds/, Available as Early as May 13, 2023, 10 pages.

Dang, V. et al., "Vessel-CAPTCHA: An efficient learning framework for vessel annotation and segmentation," Medical Image Analysis, vol. 75, Jan. 2022, 19 pages.

"3D Point Cloud Annotation," Sama Website, Available Online at https://www.sama.com/3d-lidar-radar-point-cloud-annotation/, Available as Early as May 18, 2022, 7 pages.

EP application 23220493.3 filed Dec. 28, 2023—Search Report issued Jun. 7, 2024, 8 pages.

* cited by examiner

3D INTERACTIVE ANNOTATION USING PROJECTED VIEWS

FIELD

Embodiments of the subject matter disclosed herein relate to image annotation, and more particularly to interactive 3D image segmentation.

BACKGROUND

Clinical decisions may be derived from an analysis of a set or sets within data sources. In the radiology domain, this may typically involve analysis of regions of interest from medical image data, which may include 2D or 3D medical images, such as images of organs (kidney, liver, spleen, etc.), blood vessels, bones, and the like. Medical image analysis may be performed at the request of a referring physician for a specific purpose; this purpose may include detection, assessment, and/or monitoring the progression of anatomical abnormalities like lesions, aneurysms, atrophies, and so on.

In order to access these regions of interest of the medical image data and perform the desired analysis, data corresponding to these regions may first be accurately and robustly separated from other data. While many context specific algorithms exist to segment regions of interest within medical image data, such as organs or other rounded lesions, such algorithms may produce inaccurate results, or at least consume an inordinate amount of time to produce results, for thin or elongated anatomical features or pathological structures like vessels. Moreover, factors such as scale, noise, motion, partial voluming, and other artifacts within medical image data may hamper the accuracy and precision of segmentation algorithms.

BRIEF DESCRIPTION

In one example, a method includes receiving a first segmentation input selecting a first set of pixels of a two-dimensional (2D) projected rendering, the 2D projected rendering generated from a 3D medical image dataset, retropropagating the selected first set of pixels to 3D space based on a mapping between the 2D projected rendering and the 3D medical image dataset to form a 3D segmentation mask, and saving the 3D segmentation mask in memory and/or applying the 3D segmentation mask to the 3D medical image dataset, wherein the 2D projected rendering is an intensity projection rendering.

In some examples, retropropagating the selected first set of pixels to 3D space comprises identifying one or more seed voxels in the 3D space, each seed voxel corresponding to a respective pixel of the first set of pixels; performing a 1D propagation along a ray for a selected axis starting for each seed voxel starting from the seed voxel and terminating at a slice boundary defined by the 2D projected rendering; and including each voxel along the ray in the 3D segmentation mask. In this way, interactive annotation of 2D projected renderings may increase speed and efficiency of 3D medical image data segmentation, thereby decreasing demanded processing power and increasing accuracy of such segmentations. Further, the method may be performed at least partially on a cloud-based platform, which may decrease processing power demanded by a computing device on which the annotation is performed as well as increasing efficiency of segmentation mask generation.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood from reading the following description of non-limiting embodiments, with reference to the attached drawings, wherein below.

DETAILED DESCRIPTION

Figure 1:
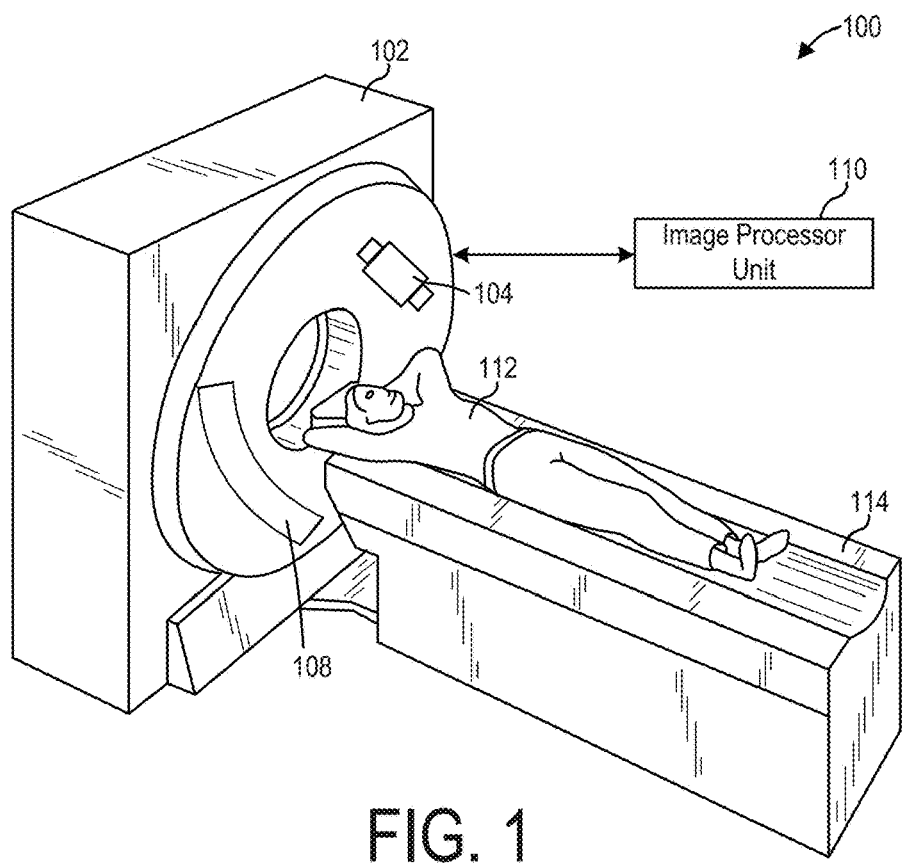
FIG. 1 shows a pictorial view of an imaging system, according to an example.

The following description relates to various embodiments for systems and methods for image segmentation of three-dimensional (3D) medical image data. Image segmentation is a sub-domain of image processing which aims at grouping similar regions or segments of an image. Image segmentation may include partitioning a digital image into distinct components (in other words, partitioning the digital image into image segments, with each image segment being a collection of pixels or voxels), and may be utilized in order to simplify and/or change the representation of an image into something that is more meaningful and easier to analyze (e.g., by a referring physician). Image segmentation may be used in a variety of applications, including use in medical imaging. During analysis of medical image data, which may be two-dimensional (2D) or 3D, it may be useful to apply segmentation to the medical image data in order to allow for easy characterization of certain anatomical features (e.g., organs, blood vessels, bones, etc.) by a referring physician for diagnosis, analysis, and the like. Current tools for image segmentation for 3D medical image data are often designed to segment rounded structures like lesions or organs but struggle to (e.g., are unable to or take a considerable amount of time to) segment thin and elongated structures like vessels and/or bones because such structures are tortuous and may branch/extend through multiple slices of 3D medical image data.

In some examples, image segmentation may be done in an automated manner, based on the medical image data and the feature desired to be segmented, via e.g., a machine learning algorithm. In other examples, segmentation may be accomplished via an image analysis algorithm, in conjunction with user interaction with the medical image data.

Machine learning or deep learning algorithms, as employed in the former type of segmentation, may make use of segmentations as ground truth data for training of the algorithms. In a context of machine learning or deep learning, ground truth refers to a reality that is to be modeled by a machine learning or deep learning algorithm. Generating large amounts of ground truth data in order to develop deep learning models is time consuming. Additionally, generating ground truth data for segmentation of elongated anatomical structures like blood vessels is often even more time consuming than for rounded structures or lesions because elongated structures may be thin and/or tortuous, and may branch throughout multiple slices of a 3D medical image.

Thus, embodiments are disclosed herein to address the above-described issues and improve segmentation of elongated anatomical structures in 3D medical image data. As will be explained in more detail below, the embodiments disclosed herein may utilize a 2D projected rendering of 3D medical image data, upon which a user may provide annotation inputs to indicate one or more regions of the 2D projected rendering that are to be included in a 3D segmentation mask of the 3D medical image data. The mask may be used to segment other medical images and/or may be stored in memory for use in training of deep or machine learning algorithms. In some examples, a 2D preview of a segmentation mask representing the 3D segmentation mask may be provided on the 2D projected rendering, which may allow the user to confirm in real-time the accuracy and extent of the 3D segmentation mask. A retropropagation algorithm may be applied to propagate the annotation inputs to 3D space and generate the 3D segmentation mask.

In this way, to segment thin, elongated anatomical structures like vessels and/or bones, the 3D medical image data may be condensed to a 2D projected rendering, which may allow increased visualization of the anatomical structures within the 3D medical image data relative to standard slices of the 3D medical image data or other 2D renderings of the 3D medical image data and thus may increase speed and efficiency of user annotation to indicate the anatomical regions to include in the segmentation process. An annotation tool may then be used by the user (e.g., a radiologist, trained annotator, or other user) to annotate the 2D projected rendering. The pixels of the 2D projected rendering selected by the user via the annotation of the 2D projected rendering may be retropropagated to the 3D space of the 3D medical image data to generate a 3D segmentation mask. As used herein, retropropagate may include back-propagating the identified structures/anatomical features (e.g., identified from the 2D projected rendering) from the 2D projected space back to the 3D space. Further, in some examples, the annotation provided by the user via the annotation tool may be used to generate a 2D preview of the 3D segmentation mask that may be displayed on the 2D projected rendering. The 2D preview may include the pixels of the 2D projected rendering selected by the user to be retropropagated to the 3D space. Annotation of the 2D rendering and generation of the 3D segmentation mask may be an iterative process, allowing the user to make changes to expand or reduce the 3D segmentation mask. Once the user determines that the 3D segmentation mask is satisfactory, the 3D segmentation mask may be saved to a memory of a computing device and optionally applied to the 3D medical image data to segment the 3D medical image data (e.g., to generate ground truth annotations or assist in clinical decision making).

Additionally, an initial segmentation mask may be used in generation of the 3D segmentation mask, wherein the initial segmentation mask is a prior mask that may be used as a template. An updated segmentation mask may then be generated via additional user inputs which are propagated to the 3D space of the initial segmentation mask to update the segmentation mask. Generation of the updated segmentation mask is based on the initial segmentation and at least one additional user input (e.g., additional annotations), and may include pre-processing of the initial segmentation (including adaptive resampling of the segmentation based on the user input from the annotation tool), and regularizing the mask update by applying a 3D low pass filter (e.g., a Gaussian filter). The updating of the segmentation as described above may then be continually iterated in real-time, in response to the user input.

In this way, segmentation of thin and/or elongated structures may be performed. Previously a difficult or time consuming process, by condensing 3D medical image data into a 2D rendering such as a Maximum Intensity Projection (MIP), a Minimum Intensity Projection (MinIP), a Volume Rendering (VR), or other suitable 2D projected rendering, receiving annotation input to the 2D rendering via an annotation tool to generate a 2D preview of a segmentation mask, and then retropropagating the data from the 2D preview to 3D space to generate a 3D segmentation mask by way of 1D propagation of seeds in the 2D preview to the 3D space, segmentation of thin and/or elongated anatomical structures can be completed relatively quickly and with fewer user inputs. Physicians may be able to easier analyze medical images and detect and diagnose anomalies of structures like vessels using these provided segmentation masks. Additionally, segmentations generated via the methods described herein may be stored and compiled as ground truth data for training deep learning models, which may allow for the ground truth data to be completed in a less time consuming manner than with traditional annotation methods. The methods herein described may increase annotation speed by allowing a user to annotate a 2D image rather than a 3D volume, may increase accuracy as less effort is needed, and may reduce frustration and/or fatigue of the user (e.g., a radiologist) performing a segmentation.

Figure 2:
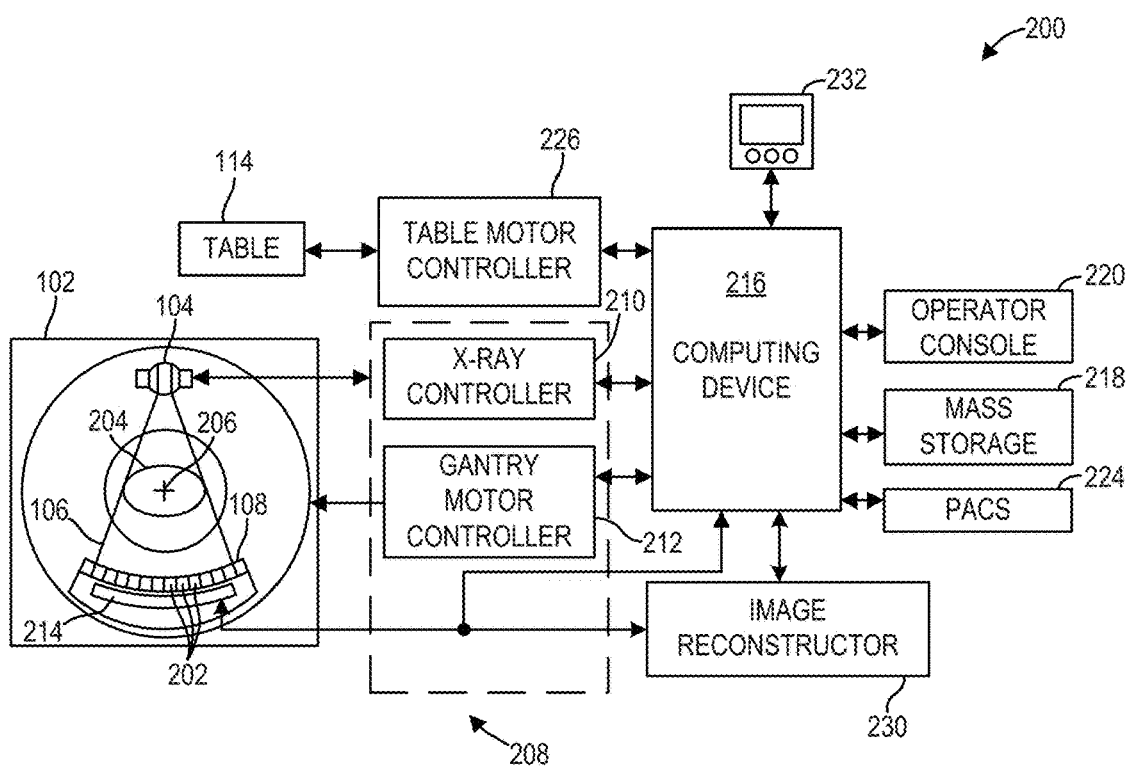
FIG. 2 shows a block schematic diagram of an example imaging system, according to an example.

The 3D volumes that may be segmented according to the embodiments disclosed herein may be generated by a single or multiple imaging modalities, including computed tomography (CT), Magnetic Resonance Imaging (MRI), and/or other modalities capable of generating volumetric imaging data (e.g., ultrasound). Image segmentation based on user input may then be enacted on the medical image data. An example imaging system that may be used to obtain 3D volumetric data for segmentation is shown in FIGS. 1-2. 3D medical image data received from an example imaging system may be segmented via use of an interactive algorithm with manual input from a user (e.g., a radiologist or other annotator). A block diagram of an example algorithm for 3D image segmentation via 2D projected rendering annotation which may be applied to the received 3D medical image data is provided in FIG. 3. An example method for generating a 3D segmentation mask from annotation data of a 2D projected rendering is provided in FIG. 4. Example user interfaces for viewing, annotating, and segmenting 3D image data via the methods herein described are shown in FIGS. 5, 6, 7A, 7B, 9, and 10. FIG. 8 illustrates an example of a 3D binary mask (e.g., a 3D segmentation mask) outputted by a segmentation process.

Embodiments of the present disclosure will now be described, by way of example, with reference to the figures. A CT imaging system is provided herein as an example imaging system that may be used to obtain data on which annotation/volume segmentation may be performed, though such annotation/volume segmentation may be executed on other suitable 3D imaging data such as MRI data, positron emission tomography (PET) data, or other suitable 3D medical imaging data. FIG. 1 illustrates an example CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an example imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, vessels, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown), a mouse, and/or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an example implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one example embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the methods described below with reference to FIGS. 3-4) described further herein may be stored as executable instructions in non-transitory memory on a computing device (or controller) in imaging system 200. In one embodiment, computing device 216 may include the instructions in non-transitory memory, and may apply the methods described herein, at least in part, to a reconstructed image after receiving the reconstructed image from image reconstructor 230. In another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

In some embodiments, one or more computing devices, for example computing device 216, PACS 224 or another image data archive, and/or another computing device configured to access 3D medical image data (e.g., a workstation coupled to a PACS (e.g., PACS 224 of FIG. 2)), may be configured for condensing 3D medical imaging data generated by the imaging system into a 2D projected rendering, wherein the 2D projected rendering projects certain voxels of 3D medical image data. The 2D projected rendering may be a MIP, a MinIP, a VR, or other suitable 2D projected rendering. Generating a MIP may entail projecting voxels of the 3D medical imaging data with the highest intensity value on each view throughout a volume of the 3D medical imaging data onto a 2D image (e.g., a 2D projected rendering). The volume herein described may include a defined thickness, e.g., a slab thickness, which is used when projecting the highest intensity voxels, wherein only voxels within that volume are considered. Generating a MinIP may entail projecting voxels of the 3D medical imaging data with the lowest intensity value on each view throughout a volume onto a 2D image. Generating a VR may entail creating a three dimensional representation of the 3D medical image data which on its own is visualized in 2D slices. The 2D projected rendering may be visualized by the user via the display 232 or the GUI instead of or alongside the 3D medical image data.

Additionally, the one or more computing devices may segment 3D medical imaging data generated by the imaging system, for use by the user via interaction with a display device and an operator console. The one or more computing devices may use an algorithm for employing annotation of a 2D projected rendering of 3D image data via user input with a 2D annotation tool such as a brush tool. The segmentation may be updated in response to user inputs with the 2D annotation tool. The user may apply the 2D annotation tool on top of the 2D projected rendering in order to annotate the 2D projected rendering to generate a 2D preview of a segmentation mask. Alternatively, the user may apply the 2D annotation tool to an initial segmentation mask in order to update or modify the segmentation mask. The 2D annotation tool may be configured to adjust the segmentation based on user input, such as add to a segmentation via a user input, such as a left click with a mouse, and to remove from a segmentation via a second type of user input, such as a right click with a mouse.

The one or more computing devices may then generate a 3D segmentation mask from the 2D preview by scanning the 3D image data for "seeds" and retropropagating the seeds back into the 3D space. Each voxel of the 3D medical image data may be known within the 2D projected rendering, including the position of each voxel with reference to the 3D space. Seed voxels, as herein described, may be voxels of the 3D medical image data which have been marked into the 2D preview of the segmentation mask based on the 2D rendering annotation. Each seed may indicate the start of a one-dimensional (1D) propagation along a ray direction in order to populate a 3D segmentation mask that may be used to segment the 3D image data. The seed voxel may be the voxel with the highest intensity along the ray for a MIP. A ray as herein described is a single ray in a particular direction. For example, for an axial 2D projected rendering, the 1D propagation may be along the Z anatomical axis (Z anatomical axis being oriented cranial-caudal). The slab thickness of the 2D projected rendering (e.g., an MIP image) may be used to constrain the propagation, whereby the propagation is extended along the ray in positive and negative directions from the seed voxel, terminating at a slice boundary defined by the defined slab thickness of the 2D projected rendering. The algorithm may then regularize the 3D mask update by applying a 3D low pass filter (e.g., a Gaussian filter).

Once the segmentation mask is complete, the segmentation mask may be stored for further use, such as to segment the 3D medical image data for use in training a machine learning or deep learning algorithm, wherein the segmentation may be used as ground truth data for training. Speed of generation of ground truth data may be increased by use of the 2D projected rendering. A method incorporating 2D projected renderings into the interactive segmentation process may decrease time needed to segment structures by allowing a user to manually annotate a single 2D projection rather than multiple slices of 3D image data.

Figure 3:
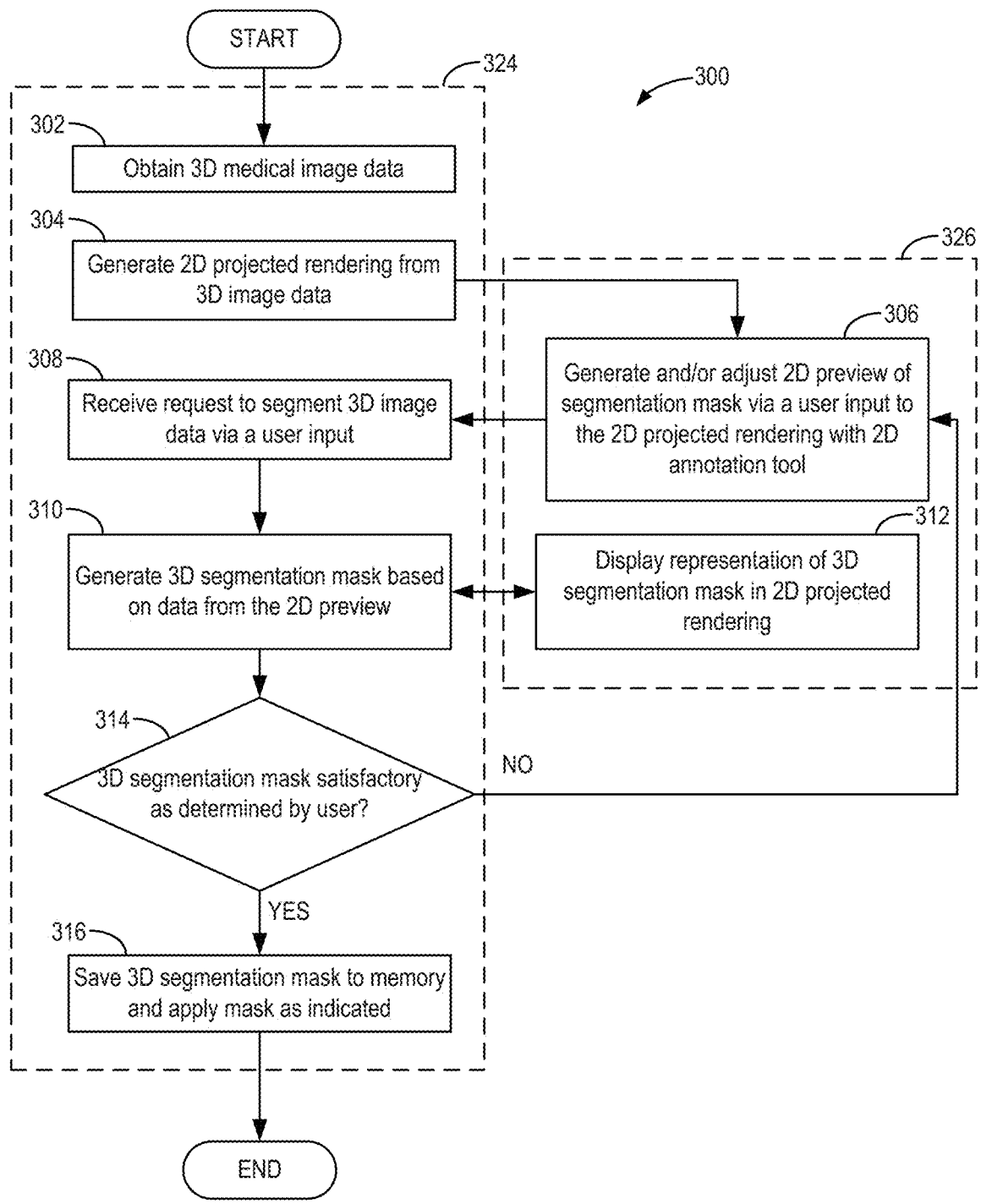
FIG. 3 shows a block diagram of a method for 3D image segmentation using a projected view.

Referring now to FIG. 3, a flowchart illustrating a method 300 for segmentation of 3D medical image data is shown. The method 300 will be described with relation to the systems depicted in FIGS. 1-2, but it should be understood that similar methods may be used with other systems without departing from the scope of this disclosure. The method 300 may be carried out via instructions stored in non-transitory memory of one or more computing devices. In some examples, the method 300 may be carried out by a client-side computing device (e.g., the computing device 216 or a PACS workstation) as well as a set of remote servers, also referred to herein as a cloud computing system, in communication with the client-side computing device. The cloud computing system may be a system that stores the 3D medical image data to be segmented (e.g., the PACS 224 or another image archive). Aspects of the method 300 that may be performed in the cloud computing system are indicated in FIG. 3 by dashed box 324. Aspects of the method 300 that may be performed on the computing device are indicated in FIG. 3 by dashed box 326. In other examples, the method 300 may be carried out on only one device, such as the client-side computing device.

At 302, the method 300 includes obtaining 3D medical image data to be segmented. The 3D medical image data may be acquired via an imaging system (e.g., imaging system 200 of FIG. 2). The 3D medical image data may include data of anatomical features of a patient that was imaged by the imaging system. In some examples, the 3D medical image data that is to be segmented may be selected based on user input. For example, a user may select a desired 3D medical image dataset to be segmented and may request, via a user input, that the selected 3D medical image dataset be segmented.

At 304, the method 300 includes generating a 2D projected rendering from the 3D medical image data. The 2D projected rendering may be a MIP, a MinIP, or another 2D projected rendering. In both MIPs and MinIPs, voxels of the 3D medical image data along respective rays are condensed to pixels within a 2D rendering for a given view (e.g., an axial view, among others). In one example in which the 2D projected rendering is a MIP, voxels of the 3D medical image data that are projected as pixels of the MIP are the voxels with the highest intensity along each ray. In another example in which the 2D projected rendering is a MinIP, voxels of the 3D medical image data that are projected as pixels of the MIP are the voxels with the lowest intensity. Each pixel within the 2D projected rendering may be known with relation to a voxel of the 3D medical image data, therefore allowing for retropropagation from the 2D projected rendering back to a dense 3D space. The 2D projected rendering may be displayed on a display (e.g., a display of computing device 216 or a display of a PACS workstation). In some examples, the 2D projected rendering may be displayed as part of a GUI that includes one or more annotation tools that may be employed to define the segmentation, as explained in more detail below.

At 306, the method 300 includes generating and/or adjusting a 2D preview of a segmentation mask via a first user input to the 2D projected rendering with a 2D annotation tool. The 2D preview may be a first segmentation input that selects a first set of pixels to be segmented. The first user input may entail a user, such as a radiologist or other annotator, manually placing the 2D annotation tool, e.g., a brush tool, on the displayed 2D projected rendering, where movement of a cursor moves the 2D annotation tool about the GUI on which the 2D projected rendering and the 2D annotation tool are displayed.

The 2D annotation tool may be a suitable annotation tool, such as a brush tool or other tool, with which the user may define which pixels of the 2D projected rendering are to be included in the segmentation, the defined pixels being included in the 2D preview. For example, the 2D annotation tool may include a highlighted region, whereby the user positions the highlighted region over a portion of the 2D projected rendering within the GUI. The 2D preview may be displayed within the highlighted region and may include an outline or overlay of one or more anatomical structures within the highlighted region of the 2D annotation tool. The 2D annotation tool, in some examples, may employ an algorithm to identify pixels within the highlighted region that should be included in the segmentation mask using computer vision or another suitable technique, such as identifying pixels that exhibit a specified range of intensity or attenuation values (e.g., between −800 and 200 Hounsfield units when the 3D medical image data is obtained with a CT imaging system) within the highlighted region. The outline or overlay of the identified pixels within the specified range of intensity values that make up the anatomical structures to be segmented may be displayed with a first color, such as blue, in order to preview the segmentation mask. Alternatively, pixels may be selected to be part of the 2D preview manually or with another annotation tool. The user may accept the identified pixels by entering a second user input, such as a mouse click, the second user input being a request to segment the pixels within the 2D preview.

At 308, method 300 includes receiving a request to segment the 3D medical image data via the user input. The second user input (e.g., a left mouse click) may indicate that the selected pixels within the 2D preview in the 2D projected rendering specified by the 2D annotation tool are to be segmented to generate the 3D segmentation mask.

At 310, method 300 includes generating the 3D segmentation mask based on data from the 2D preview. This segmentation process may be a volume segmentation that identifies selected pixels within the 2D preview and retropropagates them back into the 3D space in which the 3D medical image data was acquired, as will be further described with reference to FIG. 4.

At 312, in a real time update with 310, method 300 includes displaying within the GUI a 2D representation of the 3D segmentation mask as generated at 310. While the 2D preview of the segmentation mask may be displayed in the GUI with a first color such as blue, the 2D representation of the 3D segmentation mask following the second user input may be displayed with a second color, such as red, indicating that the structures displayed with the second color are included in the 3D segmentation mask. The 2D representation of the 3D segmentation mask may be displayed as an overlay on the 2D projected rendering in the GUI and/or on other views such as a 2D image of a slice of the 3D medical image data.

At 314, method 300 includes judging whether the 3D segmentation mask is satisfactory as determined by the user. For example, the user may enter a further user input, such as selection of a "segmentation complete" menu option, to indicate that the 3D segmentation mask is satisfactory. If the 3D segmentation mask is satisfactory, method 300 proceeds to 316, which is explained in more detail below. If the 3D segmentation mask is not satisfactory, method 300 returns to 306 to adjust the 2D preview by expanding or reducing the 2D preview in order to indicate that more or less pixels may be included in the 3D segmentation mask. Thus, method 300 may be an iterative process, wherein each second user input may be a request to segment the 3D medical image data or alter the segmentation mask. Expansion of the segmentation mask may be requested via a user input such as a left mouse click while reduction of the segmentation mask may be requested via another user input such as a right mouse click. Expansion of the segmentation mask may include adding selected pixels/voxels to the mask and reduction of the segmentation mask may include removing selected pixels/voxels from the mask.

At 316, method 300 includes saving the 3D segmentation mask to the memory of one or more of the computing devices. For example, the 3D segmentation mask may be saved as part of a patient exam in an imaging archive, such as PACS 224. In some examples, the 3D segmentation mask may be applied to the 3D medical image data to segment the 3D medical image data (e.g., generate an annotation indicating the positon of selected anatomical structures, extract voxels from the 3D medical image data corresponding to the voxels in the 3D segmentation mask, etc.). In still further examples, the 3D segmentation mask may be transmitted to one or more other computing devices. For example, the saved 3D segmentation mask may be transmitted to a remote computing device to be included in a ground truth dataset that may be used as training data for machine learning or deep learning algorithms.

Figure 4:
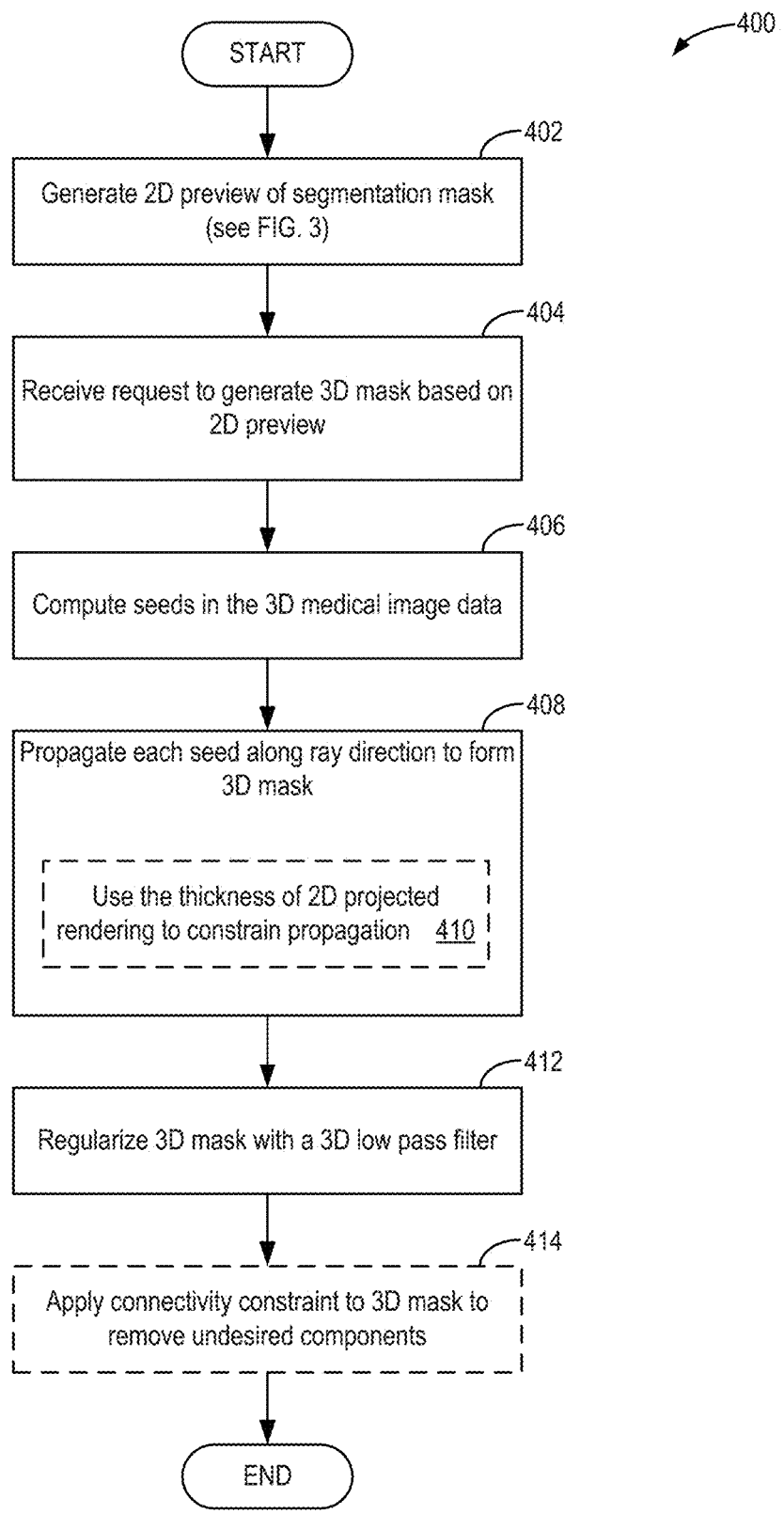
FIG. 4 shows an example of a method for generating a 3D segmentation mask from a 2D preview.

Turning now to FIG. 4, a flowchart illustrating a method 400 for volume segmentation, including retropropagation from a 2D preview of segmentation mask to a 3D segmentation mask, is shown. Method 400 may be carried out via instructions stored in non-transitory memory of a cloud computing system, such as the cloud computing system that in some examples carries out at least a portion of method 300. Method 400 may be part of the method 300 described in FIG. 3, in particular the segmentation of the 3D medical image data of 308 is described in further detail in method 400.

At 402, method 400 includes generating a 2D preview of a segmentation mask which may be performed similarly to the generation of the 2D preview of 306 of method 300. As explained previously, a 2D projected rendering may be generated from a volume of 3D medical image data, as described with reference to FIG. 3. The resultant 2D projected rendering may be annotated via user input using a 2D annotation tool, which may generate a preview of a segmentation mask (e.g., where the preview includes a selected first set of pixels of the 2D projected rendering selected by the user to be included in the segmentation), as indicated at 306 of method 300 of FIG. 3.

At 404, the method 400 includes receiving a request to generate a 3D segmentation mask based on the 2D preview displayed within the 2D projected rendering. The request may be in the form of a user input (e.g., the second user input described with reference to FIG. 3), for example a mouse click or other suitable indication via a user input device.

At 406, the method 400 includes computing and/or finding seed voxels within the 3D medical image data based on the 2D preview/selected pixels from the 2D projected rendering. The 3D medical image data may be scanned to find each seed. Each seed voxel may be a respective voxel of the 3D medical image data that was represented as a pixel in the 2D projected rendering and then marked/selected via user input into the 2D preview of the segmentation mask. Each voxel of the 3D medical image data may be mapped to a respective pixel of the 2D projected rendering such that which voxel of the 3D medical image data corresponds to which pixel of the 2D projected rendering may be known/determined. Each computed seed voxel may reside within a ray along a particular direction and multiple seeds are possible within a ray. Each identified seed voxel may have a corresponding voxel in 3D space. For example, the 3D space may be initialized with the same dimensions as the 3D medical image data (e.g., same number of voxels arranged in the same number of rows/columns). Each seed voxel of the 3D medical image data may be marked in the corresponding voxel of the 3D space.

At 408, the method 400 includes propagating each seed voxel of the 3D space along its associated ray. Propagation, in this context, includes extending or spreading a single entity (e.g., a voxel) in a direction; propagation may be done in 1D and may mark which voxels are to be included in a segmentation mask. As noted, each seed voxel resides within a ray, wherein the ray is a vector along a selected axis of the 3D space. For example, for an axial view of a MIP derived from a 3D CT dataset, a ray direction may correspond to a Z anatomical axis (e.g., where the Z anatomical axis is cranial-caudal). A point of the seed voxel may be a start of a propagation, where the propagation extends in both positive and negative directions along the ray (e.g., positive towards cranial and negative towards caudal), terminating at a slice boundary defined by the 2D projected rendering. Propagation along the ray for each seed may generate a set of voxels to be include in a segmentation mask (e.g., the 3D segmentation mask), those voxels being retropropagated into the dense 3D space of the 3D medical image data from 2D data provided, given that the relationship between the 2D data and the 3D space is known. This retropropagation generates a 3D segmentation mask from the 2D data (e.g., data of the pixels of the 2D projected rendering and the 2D preview). To provide clarification, retropropagation includes the transition of 2D data back into the 3D space while propagation, as herein used, includes marking seed voxels along an associated ray.

At 410, method 400 optionally includes constraining the propagation described at 408 based on thickness (e.g., slab thickness) of the 2D projected rendering. The 2D projected rendering, for example a MIP, may be defined with a specified thickness of the 3D medical image data that it considers. For example, the 3D medical image data (e.g., 3D CT image data) may include 2D slices with a first thickness of 0.6 mm. The MIP may be generated from a slab volume of the 3D medical image data with a second, larger thickness, such as 15 mm. As such, all voxels within multiple slices of the 3D medical image data may be condensed to a single 2D projected rendering image that displays the voxels with maximum attenuation in order to display structures more fully than the thinner slices of the 3D medical image data. The thickness of the 2D projected rendering may be specified by a user (e.g., a radiologist or annotator) and the thickness may be used to constrain the propagation at 408, whereby propagation along the ray may occur within the chosen thickness volume. Alternatively, the thickness of the 2D projected rendering may be set to consider all slices of the 3D medical image data, and as such, the seed voxels may be propagated along an entirety of a ray and may not be constrained.

At 412, the method 400 includes applying a 3D low pass filter to regularize the 3D segmentation mask. The 3D low pass filter may be a Gaussian filter or other suitable filter aimed at image denoising. Image denoising is a procedure in digital image processing aimed to remove noise from an image or segmentation mask. During image segmentation, certain elements may alter the image and leads to errors in the segmentation mask. Such elements may include: image noise, image artifacts, and tumors/lesions/high texture, among others. In particular, image noise may lead to noisy segmentations, holes in the segmentation or unnatural object boundaries, image artifacts, such as e.g., beam hardening, and scattering, may mislead the algorithms and generate noisy segmentations, and tumors/lesions/high texture may bring into the image some contours and texture that are difficult to segment manually with traditional edition tools. Regularizing the 3D segmentation mask may reduce unwanted noise in order to provide a clearer mask.

At 414, method 400 includes optionally applying a connectivity constraint to the 3D segmentation mask. Consistency between the 2D preview/pixels identified by the user as being included in the 3D segmentation mask and the 3D segmentation mask may be determined and, if desired, a connectivity constraint may exclude one or more voxels in the 3D segmentation mask not intended or wanted to be in the 3D segmentation mask as determined by the user. By use of connected components, voxels identified as unconnected to a chosen voxel may be excluded. The chosen voxel that begins the connectivity constraint may be defined by user input or by an automated algorithm. For example, when the user applies the 2D annotation tool described above, the user may place the highlighted region on a desired region of the 2D projected rendering and all pixels within the highlighted region that have an intensity value within a specified range may be selected via a user input (e.g., mouse click) to be in the 2D preview/propagated to the 3D segmentation mask. The user input that selects the pixels to be included in the 2D preview may also act to select a specific pixel (e.g., a pixel at the center point of the highlighted region when the user input was entered), and the specific pixel's corresponding voxel in the 3D segmentation mask may be the chosen voxel for applying the connectivity constraint. Starting from the chosen voxel, connected voxels may be identified and any unconnected voxels may be removed from the mask (e.g., converted from a value of 1 to a value of 0). Connected voxels may be voxels within the 3D segmentation mask along a ray with the same value (e.g., a value of 1) that are connected to the chosen voxel (directly or via intervening connecting voxels), where connectivity is predefined. As an example, 6-connectivity may be used, wherein two voxels are connected when one of six sides of a first voxel is directly adjacent to one of six sides of a second voxel. Connected voxels may be identified for each of six rays starting from the chosen voxel. When a voxel having a value of 0 is identified in a ray, all voxels having a value of 1 that come after the voxel having a value of 0 along the ray direction are determined to be unconnected to the chosen voxel and removed from the mask. In some examples, the connectivity constraint may only be applied to newly-added voxels in the mask (e.g., voxels previously added during a prior iteration of retropropagation may be ignored and left in the mask). Alternatively, if no undesired components are present, the connectivity constraint may not be applied.

Method 300 and method 400 may both be iterative processes whereby user inputs to the 2D projected rendering may repeatedly and/or continuously trigger modification of the segmentation mask. In practice, each user input via the 2D annotation brush to the 2D projected rendering may be a request to perform the algorithm for volume segmentation described with reference to method 400.

Data from segmentations performed via method 300 and method 400 and resulting segmentation masks may be saved in memory for desired downstream use, such as aiding in clinical diagnosis (whether via a clinician or computer-aided diagnosis) and/or to train machine learning or deep learning algorithms.

Figure 5:
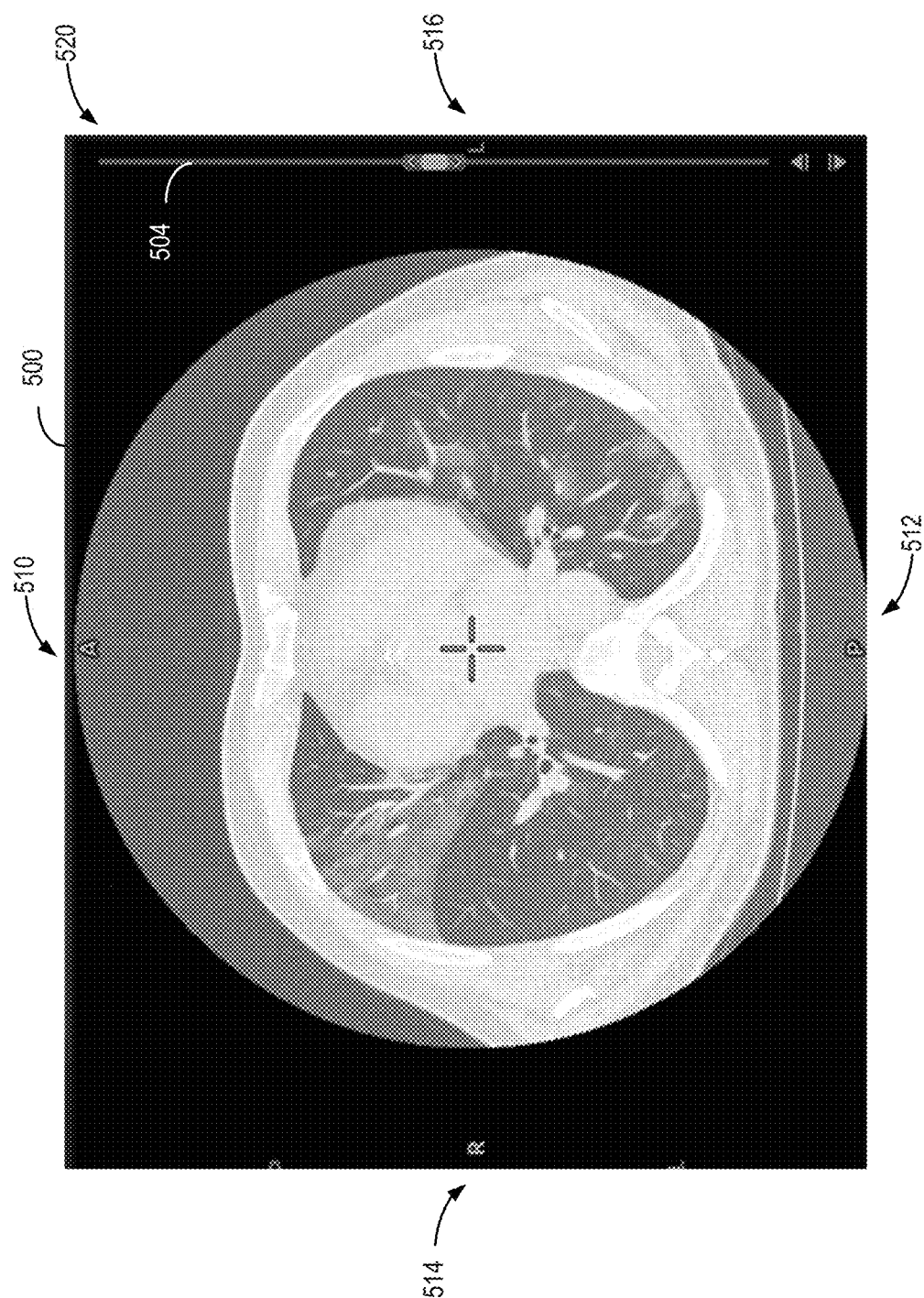
FIG. 5 shows an example slice of an example 3D medical image data.

Referring now to FIG. 5, an example medical image 500 is shown. The medical image 500 may be viewed by a user via a display of a computing device within a GUI 520. The view of medical image 500 shown in FIG. 5 is a single slice of a 3D medical image dataset, such as a CT image dataset, from an axial perspective. Orientation from the axial perspective is such that an anterior aspect of the patient is positioned at a top 510 of the GUI 520, a posterior aspect of the patient is positioned at a bottom 512 of the GUI 520, a right side of the patient is shown on a left side 514 of the GUI 520, and a left side of the patient is shown on a right side 516 of the GUI 520.

The GUI 520 further includes a scroll bar 504, which may allow a user to scroll through slices of the 3D medical image dataset. Thickness of a slice of the 3D medical image 500 may be chosen prior to image acquisition. For example, a chosen slice thickness of 0.6 mm may produce a 3D medical image dataset with more slices than a 3D medical image dataset with a chosen slice thickness of 2 mm.

In some examples, portions of anatomical structures or lesions may be visible in a single slice, but whole structures or lesions may not be visible in a single slice. For example, medical image 500 as depicted in FIG. 5 shows multiple anatomical structures, including lungs, arteries, veins, a heart, bones, and musculature. As each of these structures is three-dimensional within a body of the patient, a single slice through the structure shows the position, size, shape, and other features of the structure at only that slice. In order to visualize an entirety of a structure, the user may scroll through multiple slices. In contrast, a 2D projected rendering such as a MIP may depict the position, size, shape, and other features of the structures at multiple slices of the 3D medical image dataset as a MIP condenses multiple slices of a 3D medical image dataset into a 2D image showing the structures by projecting voxels of maximum intensity/attenuation of the 3D medical image data.

Figure 6:
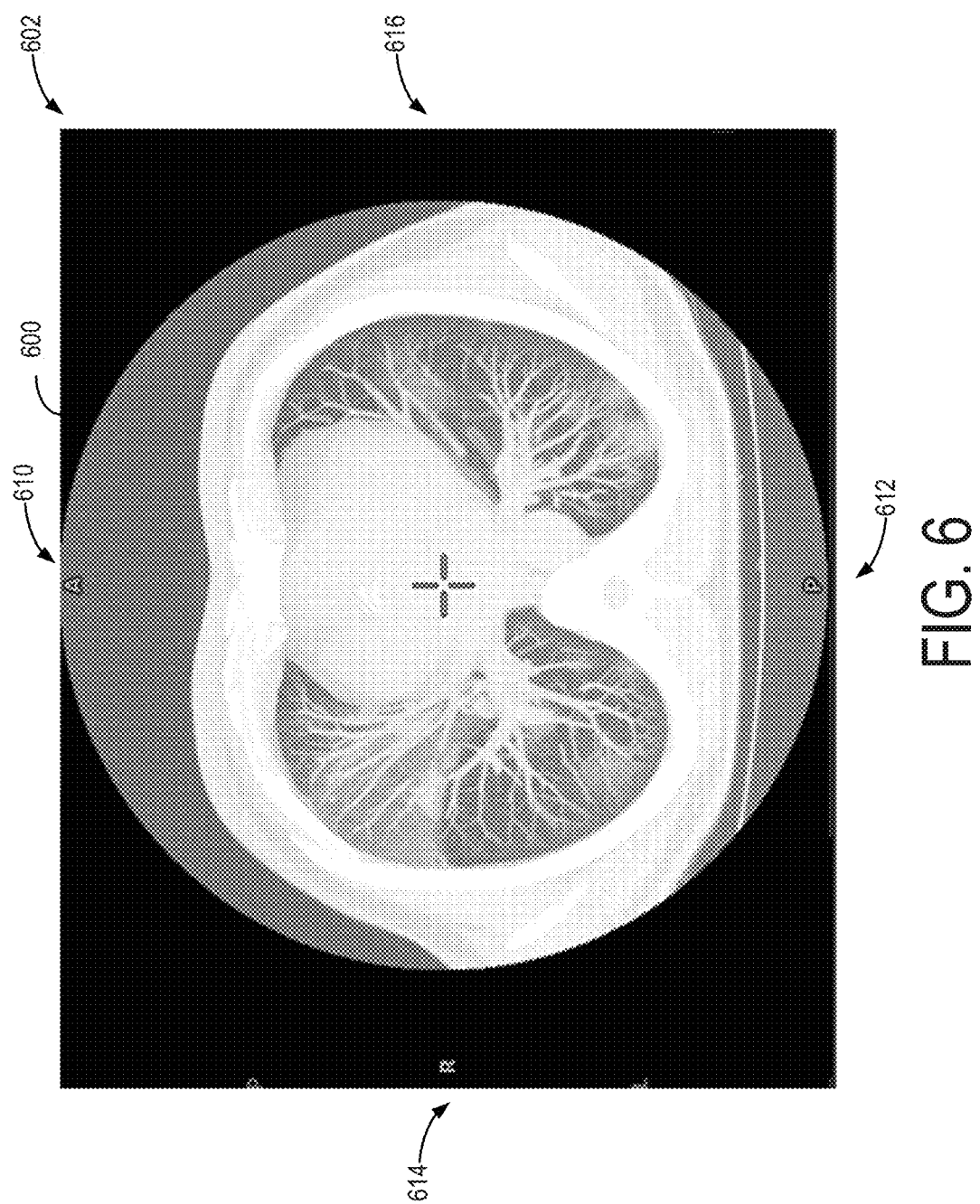
FIG. 6 shows an example 2D projected rendering of the 3D medical image data.

Referring now to FIG. 6, an example 2D projected rendering 600 is shown. 2D projected rendering 600 as depicted in FIG. 6 is a MIP, condensed from data of the 3D medical image dataset as explained above with respect to FIG. 5 (e.g., the same 3D medical image dataset from which the image 500 was generated). 2D projected rendering 600 may be displayed via a GUI 602 (e.g., GUI 520) on a display device (e.g., display 232 of FIG. 2). The 2D projected rendering 600 is depicted in FIG. 6 from an axial perspective where an anterior aspect of the patient is towards a top 610 of the GUI 602, a posterior aspect of the patient is towards a bottom 612 of the GUI 602, a right side of the patient is towards a left side 614 of the GUI 602, and a left side of the patient is towards a right side 616 of the GUI 602.

A thickness of the 2D projected rendering 600 may be defined prior to generation from the 3D medical image. The thickness may be chosen by a user as desired, the largest thickness possible being an entirety of a volume of the 3D medical image dataset. The 2D projected rendering is a 2D image and therefore no scroll bar may be present. Alternatively, in some embodiments, a scroll bar may be present in the GUI 602 in order to alter the thickness of the 2D projected rendering.

The 2D projected rendering 600 does not clearly define a foreground or a background. The anatomical structures that are not fully visible in a single slice of corresponding 3D medical image data may be visualized more fully in the 2D projected rendering than in a single slice of the 3D medical image data (or in some cases in their entirety depending on thickness of the 2D projected rendering 600). For example, a vessel of a lung which is not well visualized in a single slice of 3D medical image dataset (e.g., medical image 500 of FIG. 5) may be visualized more fully or, in some examples, in its entirety in the 2D projected rendering 600. Being able to visualize elongated structures more fully allows for a faster segmentation than when segmenting a 3D medical image alone.

Figure 7A:
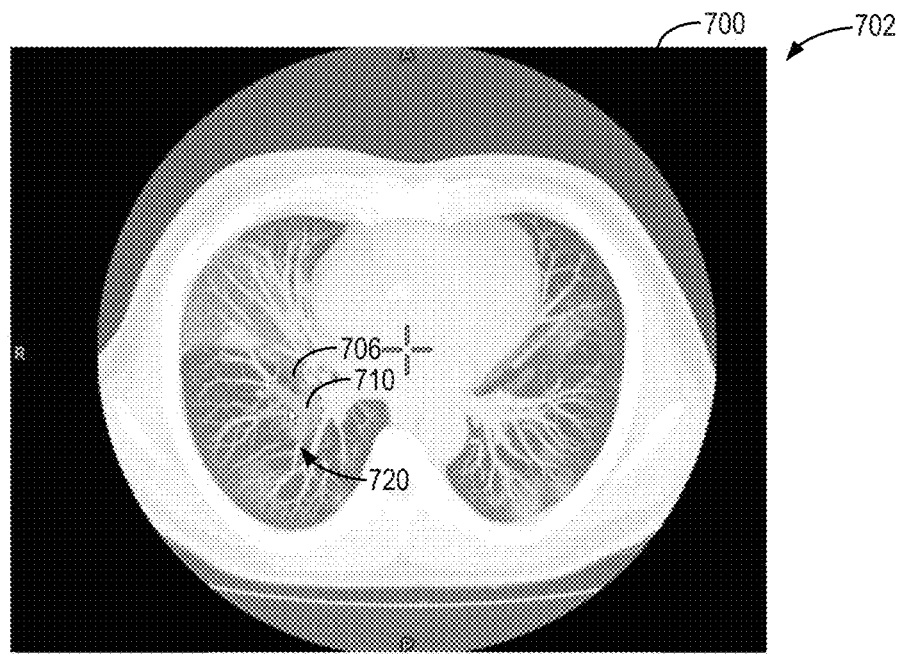
FIG. 7A shows an example graphical user interface (GUI) with an annotation tool and previewed segmentation mask.
Figure 7B:
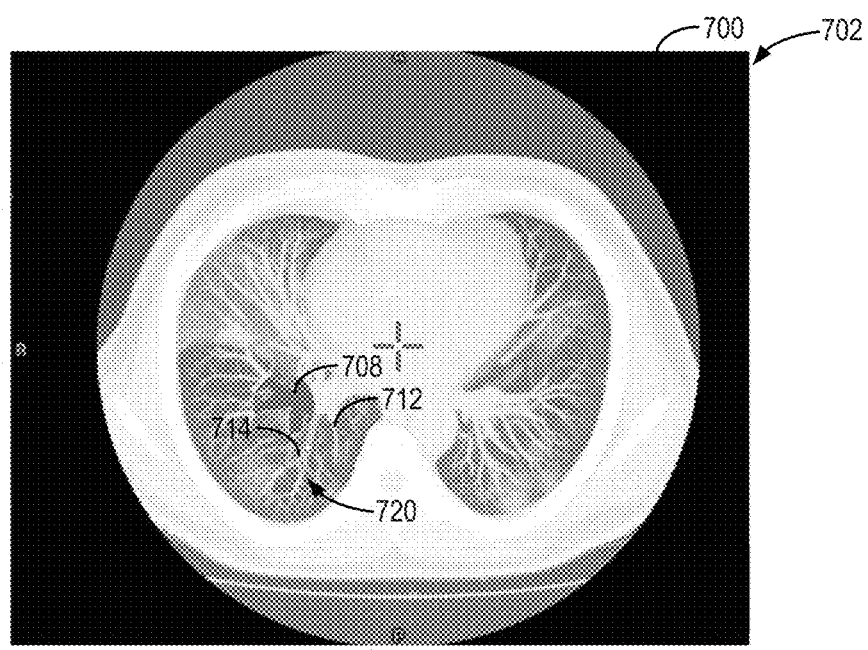
FIG. 7B shows the GUI with a representation of a 3D segmentation mask viewed in a 2D projected rendering.
Figure 8:
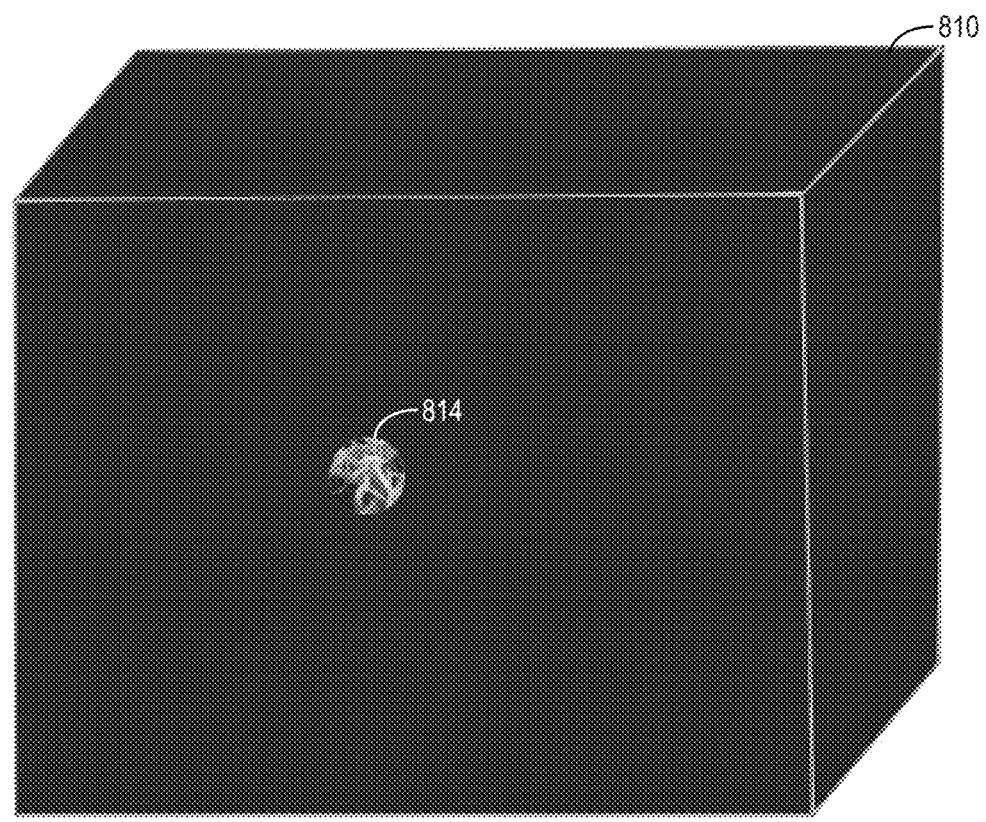
FIG. 8 shows a representation of an example binary mask.

Turning now to FIGS. 7A and 7B, an example 2D projected rendering 700 is shown. 2D projected rendering 700 may be displayed within a GUI on a display device (e.g., display device 232 of FIG. 2) prior to, during and following user annotation to a medical image.

FIG. 7A specifically depicts a 2D preview 710 within the 2D projected rendering 700. As described at 306 with reference to FIG. 3, a 2D annotation tool 720 may be used to annotate the 2D projected rendering 700, the annotation including a 2D preview 710 of a segmentation mask that may be generated upon user input. The 2D annotation tool may identify pixels within the 2D projected rendering 700 to be included in the 2D preview. In some examples, the 2D annotation tool 720 includes may include a highlighted region 706, though other examples are possible including a manual or automated annotation tool. In such examples in which a highlighted region is included with the 2D annotation tool, only structures within the highlighted region 706 may be included in the 2D preview 710. The 2D preview 710 may include an overlay (e.g., a highlight or outline) of pixels that may be included in a segmentation upon user input.

FIG. 7B specifically depicts a 2D representation 708 of a segmentation mask overlaid on the 2D projected rendering 700. The segmentation mask may be the 3D segmentation mask generated as part of a volume segmentation process. The 2D representation 708 may be generated as a result of a user input, as described at 310 with reference to FIG. 3. Specifically, 2D representation 708 may be generated as a result of a user input via the 2D annotation tool 720 to segment structures identified in the 2D preview 710 of FIG. 7A.

In some examples, a second highlighted region 712 may also be included in the GUI 702 and may include a second 2D preview 714. Upon a second user input, a second 2D representation may be generated of the structures within the second 2D preview 714. The second 2D representation may be added to 2D representation 708 to generate an updated 2D representation. The method 400 of FIG. 4 may be employed with each of these user inputs as described with reference to FIG. 4.

The 2D annotation tool 720 herein described may identify regions to be segmented in any reasonable way which may include identifying pixels based on intensity value (e.g., identifying intensity values within a specified range (e.g., −800 to 200 Hounsfield units)) or other characteristic that distinguishes pixels from one another. The specified range may be chosen by the user or may be included as a part of an automated process or algorithm. The 2D annotation tool may be configured to add components to a segmentation mask as well as remove components from a segmentation mask, for example as with an eraser feature.

Referring now to FIG. 8, an illustrative example of a 3D binary mask 810 is shown. The 3D binary mask 810 specifies a region of interest (ROI) 814 of a 2D projected rendering which may be included in a 3D segmentation mask. A binary mask as herein described identifies pixels as either included in the ROI 814 or not included in the ROI 814. Pixels of the 3D binary mask 810 with a value of one may belong to the ROI 814 and pixels of the binary mask 810 with a value of zero may not belong to the ROI 814. Pixels that are included in the ROI 814 may be depicted as white while pixels that are not included in the ROI 814 may be depicted as black (e.g., a background). Depending on the mask, the ROI 814 may contain contiguous or discontiguous groups of pixels. If the mask contains discontiguous groups of pixels and one or more of those groups is not desired to be in the mask, a connected component connectivity constraint may be applied, as described at 414 of method 400 with reference to FIG. 4.

Figure 9:
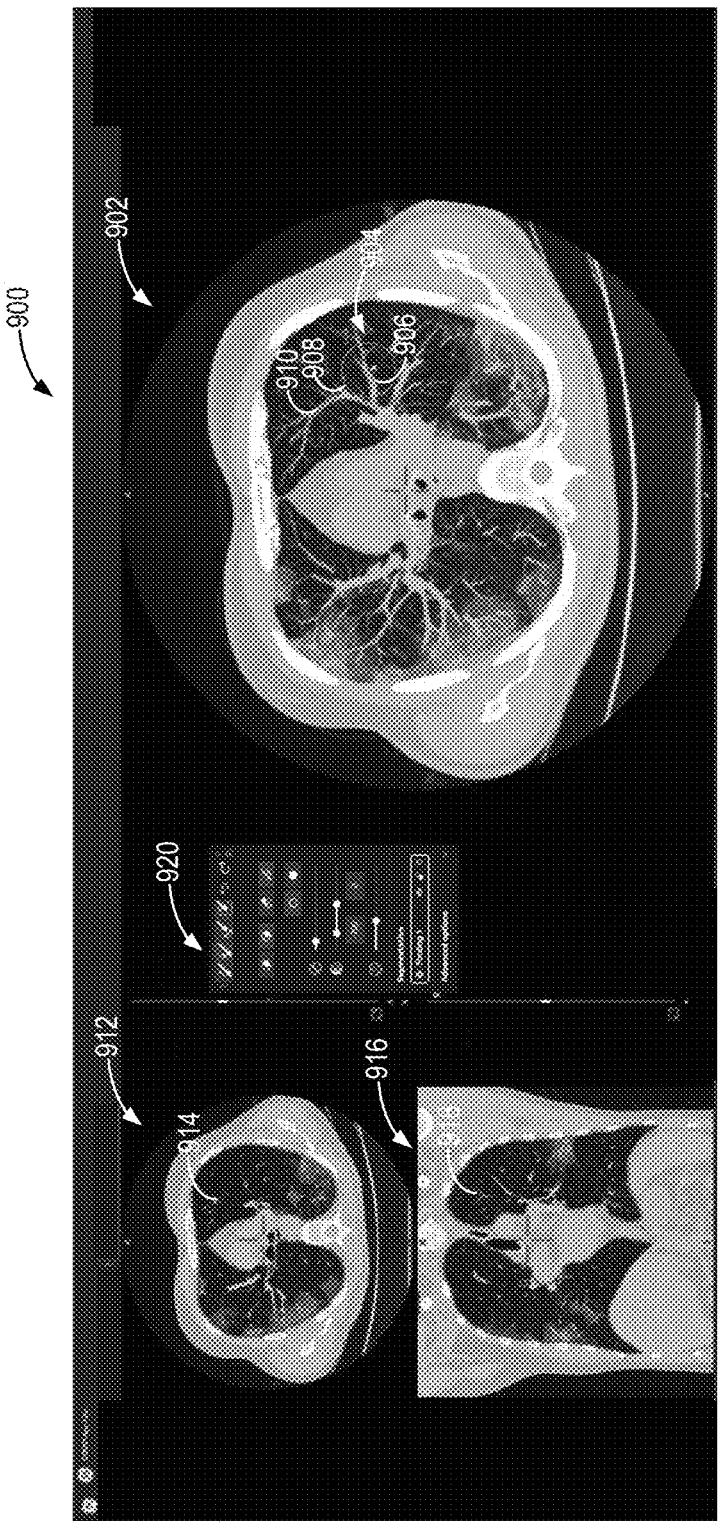
FIG. 9 shows another example GUI during annotation and segmentation of a 2D projected rendering.

Turning to FIG. 9, a GUI 900 is shown. GUI 900 may comprise a 2D projected rendering 902, a 2D annotation tool 904, and one or more views of 3D medical image data (e.g., an axial view 912 and a coronal view 916). GUI 900 may be displayed on a suitable display device (e.g., display 232 of FIG. 2). 2D projected rendering 902 may be annotated with the 2D annotation tool 904 and a resulting segmentation mask may be displayed as an overlay on the 2D projected rendering 902.

In some examples, the 2D annotation tool 904 may be a brush tool, though in other examples different annotation tools are possible. A menu 920 for the 2D annotation tool 904 may be included in the GUI 900, in which a user may choose a mode of operation and specify parameters such as intensity value ranges for the 2D annotation tool 904. The mode of operation of the 2D annotation tool 904 and the parameters may affect what types of anatomical structures may be segmented, the area of the 2D projected rendering 902 that may be segmented with a single user input, and other features.

In some examples, 2D projected rendering 902 may include a highlighted region 908 of the 2D annotation tool 904, similar to highlighted region 706 of FIG. 7A. Within the highlighted region 908, a preview 906 may be overlaid on the 2D projected rendering 902. The preview 906 may show which structures have been identified by the 2D annotation tool 904 for segmentation. Additionally, in some examples, the 2D projected rendering 902 may include a 2D representation 910 of a segmentation mask. The 2D representation 910 of the segmentation mask may have been generated as a result of user input with the 2D annotation tool 904.

The GUI 900 also comprises one or more views of the 3D medical image data that was condensed to generate the 2D projected rendering 902. The GUI 900 depicted in FIG. 9 specifically shows axial view 912 and coronal view 916 of the 3D medical image data. The axial view 912 may include a 2D representation 914 of the 3D segmentation mask, wherein the 2D representation 914 corresponds to the 2D representation 910 of the 2D projected rendering 902. The 2D representation 914 may depict a portion of the 3D segmentation mask that is visible from a particular slice of the 3D medical image data from an axial perspective. The user may scroll through slices of the 3D medical image data within axial view 912 and view the 2D representation 914 at each slice in which it is visible. A combination of all views of the 2D representation 914, each view being visible via a slice of the 3D medical image, may show the 3D segmentation mask in full form, the 3D segmentation mask having been generated based on a retropropagation algorithm as described with reference to FIG. 4.

Similarly, the coronal view 916 may include a 2D representation 918 of the 3D segmentation mask, wherein the 2D representation 918 corresponds to the 2D representation 910 of the 2D projected rendering 902 as well as the 2D representation 914 of the axial view 912. The 2D representation 918 may depict a portion of the 3D segmentation mask that is visible from a particular slice of the 3D medical image data from a coronal perspective. The user may scroll through slices of the 3D medical image data within coronal view 916 and view the 2D representation 918 at each slice in which it is visible. A combination of all views of the 2D representation 918, each view being visible via a slice of the 3D medical image, may show the 3D segmentation mask update in full form, the 3D segmentation mask update having been generated based on the retropropagation algorithm.

Thus, a user input via the 2D annotation tool 904 may generate a 2D representation of a segmentation mask as a real time update within the 2D projected rendering. As described with reference to dashed box 326 of method 300 with reference to FIG. 3, the 2D preview 906 as well as the 2D representations 910, 914, 918 may be a portion of the algorithm that is depicted within GUI 900 and as such may not be connected to a cloud computing platform. Other steps of the method 300, including the generation of the 3D segmentation mask that is represented in 2D by the 2D representations 910, 914, 918 may be a portion of the algorithm that is performed via the cloud computing platform.

Figure 10:
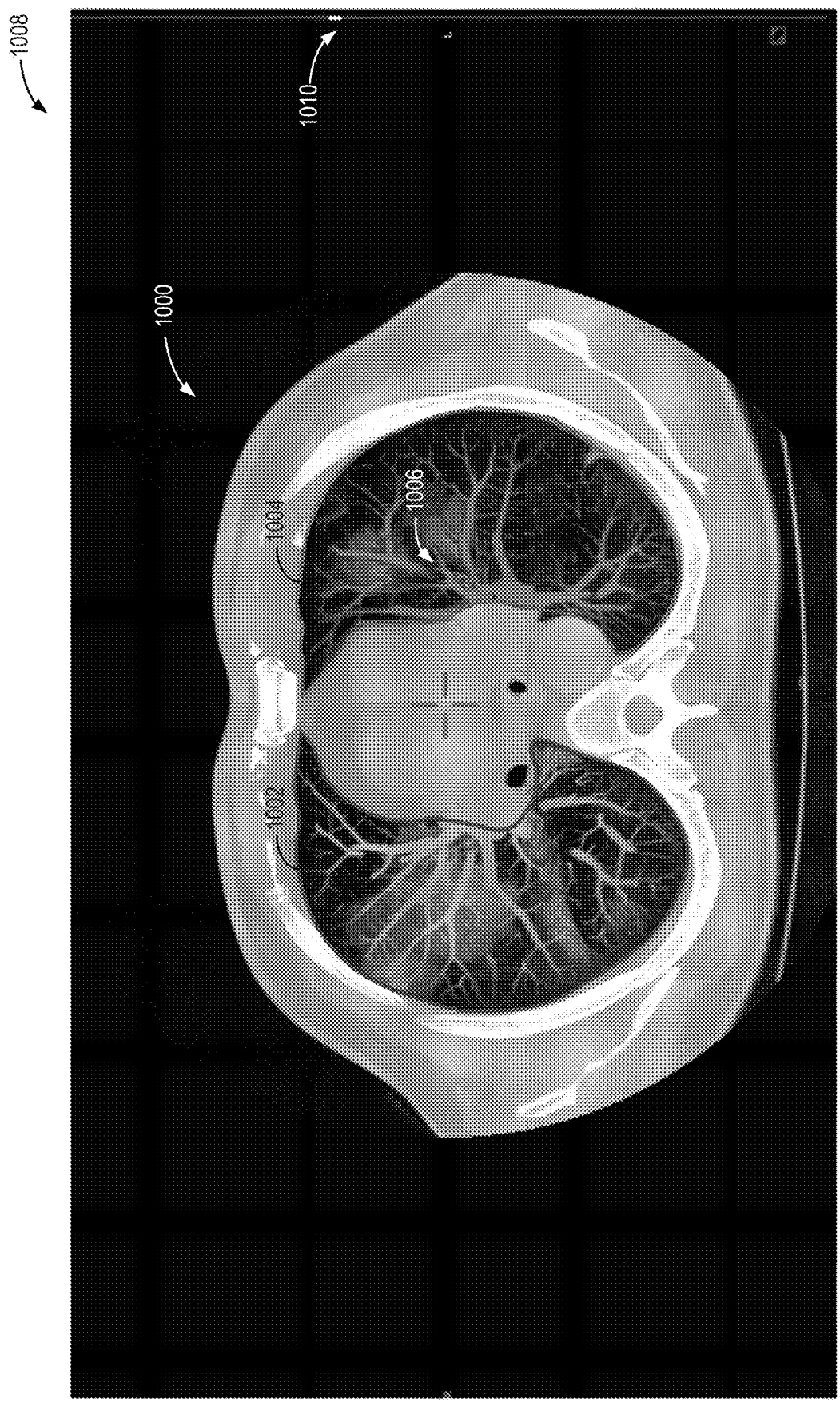
FIG. 10 shows an example GUI with multiple segmentation masks displayed.

Turning to FIG. 10, a 2D projected rendering 1000 is shown within a GUI 1008, the 2D projected rendering 1000 including one or more overlays of 2D representations of segmentation masks. A first overlay 1002 may be a representation of a first segmentation mask. In the example depicted in FIG. 10, the first overlay 1002 includes an outline of a patient's right lung from an axial perspective. A second overlay 1004 may be a representation of a second segmentation mask. In the example depicted in FIG. 10, the second overlay 1004 includes an outline of the patients left lung from an axial perspective. A third overlay 1006 may be a representation of a third segmentation mask. In the example depicted in FIG. 10, the third overlay 1006 is an overlay of vascular branchings within the patient's left lung. The third segmentation mask represented by the third overlay 1006 may be a result of a volume segmentation process such as the method described with reference to FIG. 4.

A scroll bar 1010 may be included in the GUI 1008. The scroll bar 1010 may be used to toggle between different thicknesses of the 2D projected rendering 1000. Alternatively, the scroll bar 1010 may toggle between different views, such as switching from the 2D projected rendering 1000, such as a MIP, to a multiplanar reformation (MPR) view of a corresponding 3D medical image. An MPR is a converted view of a 3D medical image, for example if a 3D medical image is acquired with axial cuts, an MPR view may be a converted coronal view or other suitable planar view.

A technical effect of the herein described systems and methods for segmentation using projected views is that increased efficiency and decreased processing power may be achieved during segmentation of thin, elongated anatomical structures. Using a middle step of a 2D projected view allows a user to annotate a single 2D image as opposed to annotating multiple slices of 3D medical image data individually. This results in reduced time spent annotating as well as reduced frustration for the user. Segmentation via a retropropagation algorithm to propagate pixels from a 2D image (e.g., the 2D projected rendering) back to a 3D space in which the 3D medical image data was acquired reduces processing power demanded by the process as opposed to a segmentation process based on the 3D medical image data alone. Using the 2D projected rendering as a middle step in the method for generating the 3D segmentation mask may avoid potential inaccurate or failed generation processes as may occur when generating a 3D segmentation mask of thin, elongated structures from a 3D image dataset alone.

Display of elements herein described, such as the selected first set of pixels (e.g., pixels within a 2D preview), as well as display of a 2D representation of the 3D segmentation mask within a GUI may allow the user to efficiently visualize the segmentation mask along with the anatomy to which it corresponds. Differentiation between the selected first set of pixels and the 2D representation may be easily denoted with colors (such as cyan versus red) within the GUI, the colors of which may be visualized as separate from the image on which they are displayed (e.g., both the selected first set of pixels and the 2D representation may be displayed as overlays on the 2D projected rendering for visualization by the user).

Further, another technical effect of the systems and methods described herein is that ground truth data for training of deep learning or machine learning models may be more quickly, efficiently, and accurately generated. As discussed, the method for retropropagation of pixels of the 2D projected rendering back to the 3D space in which the 3D medical image dataset was obtained may provide for a more efficient and accurate segmentation process. As such, more segmentation mask may be generated for a given period of time and saved to a memory for further use, therefore increasing the amount of segmentation masks available for use as ground truth data.

The disclosure also provides support for a method executable via one or more processors, comprising: receiving a first segmentation input selecting a first set of pixels of a two-dimensional (2D) projected rendering, the 2D projected rendering generated from a 3D medical image dataset, retropropagating the selected first set of pixels to 3D space based on a mapping between the 2D projected rendering and the 3D medical image dataset to form a 3D segmentation mask, and saving the 3D segmentation mask in memory and/or applying the 3D segmentation mask to the 3D medical image dataset, wherein the 2D projected rendering is an intensity projection rendering. In a first example of the method, retropropagating the selected first set of pixels to the 3D space to form the 3D segmentation mask comprises: identifying one or more seed voxels in the 3D space, each seed voxel in the 3D space corresponding to a respective pixel of the first set of pixels, for each seed voxel, performing a 1D propagation along a ray extending along a selected axis starting from the seed voxel and terminating at a slice boundary defined by the 2D projected rendering, and including each voxel along the ray in the 3D segmentation mask. In a second example of the method, optionally including the first example, the 2D projected rendering is a maximum intensity projection rendering, and wherein each pixel in the maximum intensity projection rendering represents a respective voxel of the 3D medical image dataset having a highest intensity value along an axis of the 3D medical image dataset. In a third example of the method, optionally including one or both of the first and second examples, the 2D projected rendering is a minimum intensity projection rendering, and wherein each pixel in the minimum intensity projection rendering represents a respective voxel of the 3D medical image dataset having a lowest intensity value along an axis of the 3D medical image dataset. In a fourth example of the method, optionally including one or more or each of the first through third examples, the method further comprises: applying a 3D low pass filter to the 3D segmentation mask. In a fifth example of the method, optionally including one or more or each of the first through fourth examples, the method further comprises: excluding one or more voxels from the 3D segmentation mask identified as being unconnected to a selected voxel. In a sixth example of the method, optionally including one or more or each of the first through fifth examples, the first segmentation input that selects the selected first set of pixels comprises a user input with an annotation tool, the annotation tool being configured to identify and/or select pixels within the 2D projected rendering, and further comprising receiving additional segmentation inputs selecting additional sets of pixels and iteratively retropropagating each additional set of pixels to the 3D space based on the mapping to update the 3D segmentation mask. In a seventh example of the method, optionally including one or more or each of the first through sixth examples, the first segmentation input comprises placement of a cursor to position the annotation tool over a portion of the 2D projected rendering. In a eighth example of the method, optionally including one or more or each of the first through seventh examples, retropropagation of the selected first set of pixels is triggered by a second user input, and wherein the one or more processors are part of a cloud-based platform.

The disclosure also provides support for a method, comprising: generating a two-dimensional (2D) projected rendering from a 3D medical image dataset, wherein the 2D projected rendering includes projection of a subset of voxels of the 3D medical image dataset in order to project anatomical structures from multiple slices of the 3D medical image dataset onto a 2D image, receiving a user input on the 2D projected rendering via a 2D annotation tool to preview a segmentation mask within the 2D projected rendering, generating a 3D segmentation mask based upon the user input, and saving the 3D segmentation mask to memory. In a first example of the method, the method further comprises: modifying or adjusting the 3D segmentation mask via additional user inputs to the 2D projected rendering with the 2D annotation tool. In a second example of the method, optionally including the first example, the 2D projected rendering and the 2D annotation tool are displayed via a graphical user interface (GUI), the GUI being displayed via a display device that is communicatively coupled to a computing device. In a third example of the method, optionally including one or both of the first and second examples, the method further comprises: displaying a 2D representation of the 3D segmentation mask, the 2D representation being displayed as an overlay on the 2D projected rendering within the GUI. In a fourth example of the method, optionally including one or more or each of the first through third examples, the 2D representation is displayed in a first color and the preview is displayed in a second color, different than the first color. In a fifth example of the method, optionally including one or more or each of the first through fourth examples, generating the 3D segmentation mask based upon the user input comprises: identifying one or more seed voxels within the 3D medical image dataset, wherein each of the one or more seed voxels corresponds to a pixel included in the preview of the segmentation mask, mapping the one or more seed voxels to 3D space to identify one or more corresponding seed voxels in the 3D space, and performing a one-dimensional (1D) propagation along a ray for each of the one or more corresponding seed voxels to generate the 3D segmentation mask. In a sixth example of the method, optionally including one or more or each of the first through fifth examples, additional user inputs are applied to 2D projected rendering with the 2D annotation tool to either expand or reduce the 3D segmentation mask. In a seventh example of the method, optionally including one or more or each of the first through sixth examples, the 3D medical image dataset comprises a computed tomography (CT) image dataset or a magnetic resonance imaging (MRI) image dataset, and wherein the 2D projected rendering is a maximum intensity projection (MIP), a minimum intensity projection (MinIP), or a volume rendering (VR).

The disclosure also provides support for a system for segmentation of 3D medical image data, comprising: a computing device communicatively coupled to a computed tomography (CT) system or a magnetic resonance imaging (MRI) system, either configured to generate 3D medical image data of a patient, the computing device configured with instructions in non-transitory memory that when executed cause the computing device to: generate a 2D projected rendering from the 3D medical image data, display the 2D projected rendering in a graphical user interface (GUI), select a region of interest (ROI) from the 2D projected rendering to generate a preview of a 3D segmentation mask, the ROI identified based on a user input received to the 2D projected rendering, retropropagate pixels included in the preview to 3D space to form the 3D segmentation mask of the 3D medical image data, regularize the 3D segmentation mask via a 3D low pass filter, and output the 3D segmentation mask of the 3D medical image data. In a first example of the system, the user input is applied to the 2D projected rendering via a 2D annotation tool, the 2D annotation tool being configured to identify pixels of the 2D projected rendering that are to be included in the 3D segmentation mask. In a second example of the system, optionally including the first example, a 2D representation of the 3D segmentation mask is displayed on the 2D projected rendering in real time as the 3D segmentation mask is generated and updated.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method executable via one or more processors, comprising:
   generating a two-dimensional (2D) projected rendering from a 3D medical image dataset by condensing voxels of the 3D medical image dataset into pixels based on pixel intensity;
   receiving a first segmentation input selecting a first set of pixels of the 2D projected rendering;
   retropropagating the selected first set of pixels to 3D space in which the 3D medical image dataset was acquired based on a mapping between the 2D projected rendering and the 3D medical image dataset to form a 3D segmentation mask; and
   saving the 3D segmentation mask in memory and/or applying the 3D segmentation mask to the 3D medical image dataset, wherein the 2D projected rendering is an intensity projection rendering, and wherein the mapping between the 2D projected rendering and the 3D medical image dataset comprises:
   identifying one or more seed voxels of the 3D medical image dataset in 3D space, each seed voxel in the 3D space corresponding to a respective pixel of the first set of pixels; wherein retropropagating the selected first set of pixels to the 3D space comprises:
for each seed voxel, performing a 1D propagation along a ray extending along a selected axis starting from the seed voxel and terminating at a slice boundary defined by the 2D projected rendering; and
including each voxel along each ray in the 3D segmentation mask.

2. The method of claim 1, wherein identifying the one or more seed voxels of the 3D medical image dataset in the 3D space comprises scanning the 3D medical image dataset for respective voxels of the 3D medical image dataset that were represented as pixels in the 2D projected rendering and included in the first set of pixels of the 2D projected rendering.

3. The method of claim 2, wherein the 2D projected rendering is a maximum intensity projection rendering, and wherein each pixel in the maximum intensity projection rendering represents a respective voxel of the 3D medical image dataset having a highest intensity value along an axis of the 3D medical image dataset.

4. The method of claim 2, wherein the 2D projected rendering is a minimum intensity projection rendering, and wherein each pixel in the minimum intensity projection rendering represents a respective voxel of the 3D medical image dataset having a lowest intensity value along an axis of the 3D medical image dataset.

5. The method of claim 2, further comprising applying a 3D low pass filter to the 3D segmentation mask.

6. The method of claim 2, further comprising excluding one or more voxels from the 3D segmentation mask identified as being unconnected to a selected voxel.

7. The method of claim 1, wherein the first segmentation input that selects the selected first set of pixels comprises a user input with an annotation tool, the annotation tool being configured to identify and/or select pixels within the 2D projected rendering, and further comprising receiving additional segmentation inputs selecting additional sets of pixels and iteratively retropropagating each additional set of pixels to the 3D space based on the mapping to update the 3D segmentation mask, and wherein the first segmentation input comprises placement of a cursor to position the annotation tool over a portion of the 2D projected rendering.

8. The method of claim 1, wherein the 1D propagation is constrained by a slab thickness of the 2D projected rendering.

9. The method of claim 1, wherein retropropagation of the selected first set of pixels is triggered by a second user input, and wherein the one or more processors are part of a cloud-based platform.

10. A method, comprising:
generating a two-dimensional (2D) projected rendering from a 3D medical image dataset, wherein the 2D projected rendering includes projection of a subset of voxels of the 3D medical image dataset in order to project anatomical structures from multiple slices of the 3D medical image dataset onto a 2D image for a given view;
receiving a user input on the 2D projected rendering via a 2D annotation tool to preview a segmentation mask within the 2D projected rendering;
generating a 3D segmentation mask based upon the user input; and
saving the 3D segmentation mask to memory, wherein generating the 3D segmentation mask based upon the user input comprises:
identifying one or more seed voxels within the 3D medical image dataset, wherein each of the one or more seed voxels corresponds to a pixel included in the preview of the 3D segmentation mask;
mapping the one or more seed voxels to 3D space to identify one or more corresponding seed voxels in the 3D space, wherein each of the one or more corresponding seed voxels resides within a ray along a particular direction of the given view; and
performing a one-dimensional (1D) propagation along a corresponding ray for each of the one or more corresponding seed voxels to generate the 3D segmentation mask.

11. The method of claim 10, further comprising modifying or adjusting the 3D segmentation mask via additional user inputs to the 2D projected rendering with the 2D annotation tool.

12. The method of claim 10, wherein the 2D projected rendering and the 2D annotation tool are displayed via a graphical user interface (GUI), the GUI being displayed via a display device that is communicatively coupled to a computing device.

13. The method of claim 12, further comprising displaying a 2D representation of the 3D segmentation mask, the 2D representation being displayed as an overlay on the 2D projected rendering within the GUI.

14. The method of claim 13, wherein the 2D representation is displayed in a first color and the preview is displayed in a second color, different than the first color.

15. The method of claim 10, wherein the 1D propagation is constrained by a slab thickness of the 2D projected rendering.

16. The method of claim 10, wherein additional user inputs are applied to 2D projected rendering with the 2D annotation tool to either expand or reduce the 3D segmentation mask.

17. The method of claim 10, wherein the 3D medical image dataset comprises a computed tomography (CT) image dataset or a magnetic resonance imaging (MRI) image dataset, and wherein the 2D projected rendering is a maximum intensity projection (MIP), a minimum intensity projection (MinIP), or a volume rendering (VR).

18. A system for segmentation of 3D medical image data, comprising:
a computing device communicatively coupled to a computed tomography (CT) system or a magnetic resonance imaging (MRI) system, either configured to generate 3D medical image data of a patient, the computing device configured with instructions in non-transitory memory that when executed cause the computing device to:
generate a 2D projected rendering from the 3D medical image data, wherein the 2D projected rendering comprises pixels condensed from a subset of voxels of the 3D medical image data, each of the subset of voxels residing within a ray;
display the 2D projected rendering in a graphical user interface (GUI);
select a region of interest (ROI) from the 2D projected rendering to generate a preview of a 3D segmentation mask, the ROI identified based on a user input received to the 2D projected rendering;
retropropagate pixels included in the preview to 3D space to form the 3D segmentation mask of the 3D medical image data;
regularize the 3D segmentation mask via a 3D low pass filter; and output the 3D segmentation mask of the 3D medical image data, wherein retropropagating pixels included in the preview to 3D space comprises:
    finding one or more seed voxels within the 3D medical image data based on pixels of the selected ROI, wherein each of the one or more seed voxels is one of the subset of voxels of the 3D medical image data; and
    propagating each of the one or more seed voxels along an associated ray to generate a set of voxels to be included in the 3D segmentation mask.

19. The system of claim 18, wherein the user input is applied to the 2D projected rendering via a 2D annotation tool, the 2D annotation tool being configured to identify pixels of the 2D projected rendering that are to be included in the 3D segmentation mask.

20. The system of claim 18, wherein a 2D representation of the 3D segmentation mask is displayed on the 2D projected rendering in real time as the 3D segmentation mask is generated and updated.

* * * * *